United States Patent [19]

Sizto et al.

[11] Patent Number: 4,791,056
[45] Date of Patent: Dec. 13, 1988

[54] CALIBRATION DEVICE FOR HETEROGENEOUS IMMUNOASSAY

[75] Inventors: N. Chung Sizto, Palo Alto; Cynthia G. Roux, Foster City, both of Calif.

[73] Assignee: Syntex (U.S.A.) Inc., Palo Alto, Calif.

[21] Appl. No.: 593,762

[22] Filed: Mar. 27, 1984

[51] Int. Cl.$^4$ .................. G01N 33/577; G01N 33/545
[52] U.S. Cl. ............................................ 435/7; 435/4; 435/188; 435/805; 435/810
[58] Field of Search .................. 435/4, 7, 188, 810, 435/805

[56] References Cited

U.S. PATENT DOCUMENTS

| | | | |
|---|---|---|---|
| 4,230,683 | 10/1980 | Decker et al. | 436/804 |
| 4,366,241 | 12/1982 | Tom et al. | 435/7 |
| 4,533,629 | 8/1985 | Litman et al. | 436/810 |
| 4,540,659 | 9/1985 | Litman et al. | 436/525 |

FOREIGN PATENT DOCUMENTS 2098730  11/1982  United Kingdom .................. 435/7

OTHER PUBLICATIONS

Litman et al., Clin. Chem., 29(1983), 1598–1603.

*Primary Examiner*—Christine M. Nucker
*Attorney, Agent, or Firm*—Theodore J. Leitereg

[57] ABSTRACT

A device is disclosed for use in a simultaneous calibration assay method wherein a conjugate of a catalyst and a member of a specific binding pair ("mip") is employed. The present device comprises a surface to which a receptor is non-diffusively bound. The receptor is capable of specific binding to the conjugate of the catalyst and mip and is substantially incapable of binding to the catalyst or the mip apart from the conjugate. The surface may be an integral part of, or separate from, a support.

19 Claims, No Drawings

CALIBRATION DEVICE FOR HETEROGENEOUS IMMUNOASSAY

BACKGROUND OF THE INVENTION

1. Field of the Invention

There is continuing interest in developing new, simpler and more rapid techniques to detect and measure the presence of an analyte in a sample. The analyte may be any of a wide variety of materials, such as drugs, naturally occurring physiological compounds, pollutants, chemicals, contaminants, or the like. In many cases, speed is important for the measurement, particularly with certain physiologically active compounds. In other situations, convenience can be a major consideration.

One convenient and rapid technique which has found wide application is the use of an immunochemical strip, generally comprising a solid rod or film which can be dipped in a sample and subsequently processed to produce a signal based on the amount of analyte in the original sample. There is ample instrumentation to measure a signal, such as light absorption, reflectance or fluorescence produced by a compound bound to a solid surface. Also the immunochemical strip allows for convenient handling, transfers, separations, and the like.

Although convenient, such techniques are highly sensitive to development time, temperature, interfering factors, reagent stability and other conditions which may affect the level of the observed signal.

Accurate detection of an analyte in a sample which is largely insensitive to development time, temperature, interfering factors in the sample, and the like has been achieved (U.S. Ser. Nos. 374,849, filed May 4, 1982, and 399,107, filed July 16, 1982). The method and apparatus involve first and second surfaces, referred to as measurement and calibration surfaces, each involving a signal producing system having at least one catalyst and one substrate, where the systems are substantially the same and involve the same catalyst.

The measurement surface involves the binding of a catalyst conjugate to the surface by means of specific binding pair complex formation associated with the analyte. The amount of catalyst which binds to the surface is related to the amount of analyte in the assay medium.

The calibration surface has a catalyst bound to the surface through the intermediacy of specific binding pair complex formation, where the specific binding pair is different from the binding pair of the measurement surface.

By comparison of the level of signal generating compound at each surface, one can determine whether the amount of analyte is greater or lesser than a predetermined amount, which amount is indicated by the signal generated from the calibration surface.

2. Brief Description of the Prior Art

Patents concerned with various immobilized reagents and different types of test strips include U.S. Pat. Nos. 3,993,451; 4,038,485; 4,046,514; 4,129,417; 4,133,639; and 4,160,008, 4,299,916, and German Offen. No. 2,636,244. Patents disclosing a variety of methods involving separations of bound and unbound antigen include U.S. Pat. Nos. Re. 29,169; 3,949,064; 3,984,533; 3,985,867; 4,020,151; 4,039,652; 4,067,959; 4,108,972; 4,145,406; and 4,168,146.

U.S. Ser. Nos. 374,849, filed May 4, 1982, and 399,107, filed July 16, 1982, are directed to a simultaneous calibration heterogeneous immunoassay.

SUMMARY OF THE INVENTION

A device is disclosed for use in a simultaneous calibration assay method wherein a conjugate of a catalyst and a member of a specific binding pair ("mip") is employed. The present device is an improvement in the known calibration surface and comprises a surface to which a receptor is non-diffusively bound. The receptor is capable of specific binding to the conjugate of the catalyst and a mip and is substantially incapable of binding to the catalyst or the mip apart from the conjugate. The surface may be an integral part of, or separate from, a support.

DESCRIPTION OF THE SPECIFIC EMBODIMENTS

The present invention provides for an improvement in the calibration surface of the known method as described in U.S. Ser. Nos. 374,849, filed May 4, 1982, and 399,107, filed July 16, 1982.

The device of the present invention comprises a surface to which a receptor is non-diffusively bound. The receptor bound to the surface is capable of specific binding to a conjugate of the catalyst and a mip (catalyst-bound-mip) and is substantially incapable of binding to the catalyst apart from the conjugate or to the mip apart from the conjugate.

The known simultaneous calibration assay method is useful for the determination of the presence of an analyte in a sample. The analyte is a member of a specific binding pair consisting of ligand and receptor ("antiligand"). The known method comprises combining a measurement surface and a sample suspected of containing an analyte in an aqueous assay medium. Simultaneously therewith or successively thereafter the measurement surface is combined with members of a signal producing system. The system includes at least a conjugate of a mip and a label which provides an amount of a signal generating compound at the measurement surface related to the amount of analyte in the assay medium. A calibration surface is present in the assay medium. The calibration surface provides a signal level from the signal generating compound as a result of at least one ligand-receptor binding involving mip conjugated to a label where the mip associated with the calibration surface is different from the mip associated with the measurement surface. The ratio of the signal at the calibration surface to that at the measurement surface relates to the amount of analyte in the sample substantially independent of non-specific factors.

The above method provides for simultaneous calibration of the assay system during the performance of each individual test. The signal producing system as it relates to the production of a detectable signal at the two surfaces is subject to a number of the same conditions which affect the observed detectable signal. Thus, variations in the production of a detectable signal due to variations in conditions, endogenous materials in the sample, or the like, will affect the production of the detectable signal in parallel ways. The signal level of the calibration surface serves as a standard for the evaluation of the signal level of the measurement surface.

In the known method, a mip that differs from that associated with the measurement surface is employed on the calibration surface. The mip on the calibration surface binds to either the catalyst portion or to the mip portion of the catalyst-mip conjugate. The measurement surface includes the specific binding partner for the mip that forms part of the catalyst-mip conjugate. The production of the detectable product which produces the signal on the surface will be directly related to the amount of the catalyst which becomes bound to the measurement surface. By contrast, the amount of catalyst which binds to the calibration surface will not be solely dependent upon, and may be independent of, the amount of analyte in the medium.

Once the catalyst molecules are bound to the surfaces, the catalytic activity or turnover rate at the two surfaces will be subject to the same environment, so that the production of detectable product on the calibration surface can be used as a basis for a qualitative or quantitative determination of the concentration of analyte in the medium.

Certain advantages have been found for a calibration surface in accordance with the present invention, which surface includes a receptor that is capable of binding to the conjugate of the catalyst and the mip and is substantially incapable of binding to the catalyst or the mip apart from the conjugate. These advantages are explained as follows: A conjugate of a catalyst and a mip generally includes one or more mips bound to the catalyst. In many situations, the catalyst-bound-mip is unstable and may dissociate into a conjugate containing fewer mips or no mips at all. In the simultaneous calibration assay, the calibration surface contains a predetermined amount of a mip ("calibration" mip). The measurement surface contains the specific binding partner for the mip of the catalyst-mip conjugate. By comparing the signals generated at the two surfaces, one can determine whether the amount of analyte is greater or less than the predetermined amount.

The predetermined amount of calibration mip is predicated on a catalyst-bound-mip conjugate that remains intact. Where the conjugate dissociates partially or wholly, there is less or no chance for the conjugate to become bound to the measurement surface. This means that catalyst becomes less likely to become attached to the measurement surface. Where the mip on the calibration surface is specific for the catalyst, this mip will bind to catalyst whether or not it is part of the conjugate. Consequently, the predetermined ratios giving specific signal levels become distorted leading to an inaccurate assay.

The subject invention will now be described in greater detail. However, before describing the invention in detail, a number of terms will be defined.

DEFINITIONS

Analyte—the compound or composition to be measured, which may be a ligand, which is mono- or polyepitopic, usually antigenic or haptenic, a single or plurality of compounds which share at least one common epitopic or determinant site, or a receptor.

The polyepitopic ligand analytes will normally be poly(amino acids), i.e., polypeptides and proteins, polysaccharides, nucleic acids, and combinations thereof. Such combinations include bacteria, viruses, chromosomes, genes, mitochondria, nuclei, cell membranes and the like.

The precise nature of the analytes together with numerous examples thereof are disclosed in U.S. Pat. No. 4,299,916 to Litman, et al., particularly columns 16 to 23, the disclosure of which is incorporated herein by reference.

Member of a specific binding pair ("mip")—one of two different molecules, having an area on the surface or in a cavity which specifically binds to a particular spatial and polar organization of the other molecule. The members of the specific binding pair are referred to as ligand and receptor (antiligand). These will usually be members of an immunological pair, although other specifically binding pairs such as biotin-avidin, hormones-hormone receptors, and the like are not immunological pairs. Homologous or complementary substances are ligand and receptor, while analogous substances are either ligands or receptors, which are differentiated in some manner, e.g., labeling.

Ligand—any organic compound for which a receptor naturally exists or can be prepared.

Receptor (antiligand)—any compound or composition capable of recognizing a particular spatial and polar organization of a molecule, i.e., epitopic or determinant site. Illustrative receptors include naturally occurring receptors, e.g., thyroxine binding globulin, antibodies, enzymes, Fab fragments, lectins, nucleic acids and the like.

Conjugate receptor—any compound or composition capable of specific binding to a conjugate of a catalyst and a mip and substantially incapable of binding with the catalyst or the mip apart from the conjugate. The conjugate receptor differs from the analyte and its homologous specific binding pair member. Preferably, the conjugate receptor is capable of recognizing a particular spatial and polar organization, i.e., an epitopic or determinant site, in the area of the conjugative link between the catalyst and the mip.

Ligand analog—a modified ligand which can compete with the analogous ligand for a receptor, the modification providing means to join a ligand analog to another molecule. The ligand analog will usually differ from the ligand by more than replacement of a hydrogen with a bond which links the ligand analog to a hub or label, but need not.

Poly(ligand analog)—a plurality of ligands or ligand analogs covalently joined together, normally to a hub nucleus. The hub nucleus is a polyfunctional material, normally polymeric, usually having a plurality of functional groups, e.g., hydroxy, amino, mercapto, ethylenic, etc., as sites for linking. The hub nucleus is normally water soluble or at least dispersible add will usually be at least about 35,000 daltons, but generally not exceeding about 600,000 daltons. Illustrative hub nuclei include polysaccharides, polypeptides, including proteins, nucleic acids, ion exchange resins and the like.

Surface—the measurement and calibration surfaces will each be non-dispersed and have an available surface area of at least about 50 $\mu m^2$ and generally greater, often at least about 1 $mm^2$, usually being on a common support, particularly when less than about 0.5 $cm^2$, and may be of any material which is insoluble in water and provides the necessary properties for binding of a mip and a detectable signal generating compound to provide a desired signal level. Desirably, the surface will be gelatinous, permeable, bibulous, porous or have a rough or irregular structure, which may include channels or indentations, generally having a substantial void volume as compared to total volume. Depending upon the nature of the detectable signal generating compound, the surface will be adsorbent or non-adsorbent, preferably being weakly or non-adsorbent. The surface may be transparent or opaque, a single material or a plurality of materials, mixtures or laminates. A wide variety of materials and shapes may be employed. The surface will be capable of substantially retaining its integrity under the conditions of the assay, so that substances which are bound to the surface will remain bound to the surface and not diffuse into solution. It is desirable that underlying structures of both the measurement and calibration surfaces be substantially identical.

Catalyst-bound-mip—catalyst, usually an enzyme, conjugated to a mip. The catalyst is a member of the signal producing system and the mip is chosen to bind to the measurement surface in accordance with the particular protocol.

Signal-producing system—the signal-producing system includes at least one catalyst, usually at least one enzyme, and at least one substrate and may include two or more catalysts and a plurality of substrates, desirably including a combination of enzymes, where the substrate of one enzyme is the product of the other enzyme. The operation of the signal producing system is to produce a product which provides a detectable signal at the measurement surface related to the amount of catalyst bound to that surface, as a result of mip complex formation of the catalyst-bound-mip. The signal producing system, employed in whole or part at the calibration surface, also produces a detectable signal at the calibration surface. The level of the detectable signal is dependent on at least one factor independent of the amount of analyte. Other materials which may be included in the signal producing system include scavengers for an intermediate product, where a plurality of enzymes are employed.

The signal producing system provides for the production of a compound, which is normally the signal generating compound, but in some instances may react with another compound bound to the surfaces with the production, enhancement or destruction of the signal generating compound. While both enzymatic and non-enzymatic catalysts may be employed, usually there will be at least one enzyme catalyst employed in the signal producing system. In the event of there being only one catalyst, this catalyst will be conjugated to a mip for binding to the measurement surface through complex formation. In addition to the catalyst, there must be a solute which undergoes a transformation which results in a change in a detectable signal at the measurement surface.

For the most part, the product resulting from the transformation catalyzed by the catalyst-bound-mip will be the signal generating compound. Therefore, where there is only one catalyst, usually an enzyme, the signal producing system will involve the catalyst-bound-mip and its substrate.

Preferably, two catalysts will be employed, either a combination of an enzyme and a non-enzyme catalyst or two enzymes, where the two catalysts are related in that the product of one is the substrate of the other. In this system, there need be only one solute or substrate which can undergo successive changes catalyzed by the catalysts, which results in the compound involved with production of a detectable signal. For the most part, however, there will normally be a substrate for the first enzyme in the series and a second compound, which serves as a precursor to the compound involved in the production of the signal, normally providing the compound which produces the signal. Thus, the product of the first enzyme may react with the precursor to the signal producing compound to provide the signal generating compound.

For the most part, the involved reactions will be hydrolysis or redox reactions. In the case of hydrolysis, substitution of a dye by a water solubilizing compound joined by an enzymatically labile bond, where two enzymatic steps are required to result in the insoluble dye product, is illustrative of this type of system. By contrast, in redox reactions, the first enzyme can produce an essential substrate for the second enzyme, where the second enzyme catalyzes the reaction between the product of the first enzyme and the dye precursor.

The enzymatic reaction may involve modifying the solute to a product which is the substrate of another enzyme or production of a compound which does not include a substantial portion of the solute, which serves as an enzyme substrate. The first situation may be illustrated by glucose-6-phosphate being catalytically hydrolyzed by alkaline phosphatase to glucose, where glucose is a substrate for glucose oxidase. The second situation may be illustrated by glucose being oxidized by glucose oxidase to provide hydrogen peroxide which would enzymatically react with the signal generator precursor to produce the signal generator.

Coupled catalysts can also involve an enzyme with a non-enzymatic catalyst. The enzyme can produce a reactant which undergoes a reaction catalyzed by the non-enzymatic catalyst or the non-enzymatic catalyst may produce a substrate (includes coenzymes) for the enzyme. A wide variety of non-enzymatic catalysts which may be employed in his invention are found in U.S. Pat. No. 4,160,645, issued July 10, 1979, the appropriate portions of which are incorporated herein by reference.

Various combinations of enzymes may be employed to provide a signal generating compound at the surface. Particularly, combinations of hydrolases may be employed to produce an insoluble signal generator. Alternatively, combinations of hydrolases and oxidoreductases can provide the signal generating compound. Also, combinations of oxidoreductases may be used to produce an insoluble signal generating compound. The following table is illustrative of various combinations which may be employed to provide for preferential production of the signal generating compound at the surface. Usually there will be a preferred catalyst at the surface, since as indicated previously, by appropriate choice of the catalyst at the surface, a greater number of reagents may be combined in a single formulation.

For a more detailed discussion of the signal producing system and illustrative examples, see U.S. Ser. No. 374,849, filed May 4, 1982 now U.S. Pat. No. 4,533,629.

Ancillary Materials—Various ancillary materials will frequently be employed in the calibration assays. Particularly, enzyme substrates, cofactors, activators, scavengers, inhibitors or the like may be included in the assay medium.

In addition, buffers will normally be present, as well as stabilizers. Frequently in addition to these additives, additional proteins may be included, such as albumins; or surfactants, particularly non-ionic surfactants, e.g., polyalkylene glycols, or the like.

Device

The device of the present invention for use in a simultaneous calibration assay comprises a surface to which a conjugate receptor is non-diffusively bound. The conjugate receptor is normally an antibody specific for the conjugate of the catalyst and the mip (catalyst-bound-mip). This antibody is further characterized in that it is substantially incapable of binding with the catalyst apart from the conjugate and is substantially incapable of binding to the mip apart from the conjugate.

Particularly preferred as a conjugate receptor is a monoclonal antibody specific for the conjugate. For the most part, such a monoclonal antibody will be capable of specific binding to the conjugate at a site comprising the linking group through which the catalyst and mip are bound. The monoclonal antibody will be substantially incapable of binding to the catalyst or the mip apart from the conjugate.

Polyclonal and monoclonal antibodies useful as conjugate receptors in the present invention may be prepared according to techniques well-known in the art. Polyclonal antibodies may be raised in a suitable host after challenge with an appropriate antigen and may be collected in the standard manner.

Monoc-lonal antibodies may be prepared by the process discussed by Milstein and Kohler, *Nature,* 256, 495–497 (1975). The details of that process are well-known and will not be repeated here. However, basically the process involves injecting a mouse, or other suitable animal, with an immunogen. The mouse is subsequently sacrificed, and cells taken from its spleen are fused with myeloma cells. The result is a hybrid cell, referred to as a "hybridoma," that reproduces in vitro. The population of the hybridomas is screened to isolate individual clones, each of which secrete a single antibody species to the antigen. The antibody species are screened to select those which have the characteristics useful in the present invention, namely, those which are capable of binding to a conjugate of a catalyst and a mip and substantially incapable of binding to the catalyst apart from the mip.

The underlying surface to which the conjugate receptor is attached to form the calibration surface can vary widely. Generally, the underlying surface will be the same for both the calibration and the measurement surfaces. Normally, the surface is chosen so as not to be strongly absorbent for members of the signal producing system to minimize interference with the assay. The underlying structure of the surface may take different forms, have different compositions and may be a mixture of compositions or laminates or combinations thereof. The material chosen for the surface must be able to interact with the signal generating compound by desolubilization of the signal generating compound or complexation reaction or interaction of another compound bonded to the surface, so as to form, destroy or interact with the signal generating compound.

The surface may assume a variety of shapes and forms and may have varied dimensions, depending on the manner of use and measurement. Illustrative surfaces may be pads, discs, or strips which may be flat, concave or convex. The thickness is not critical, generally being from about 0.1 to 2 mm thick and of any convenient diameter or other dimensions. Typically, the calibration surface and the measurement surface will be supported on a common member, such as a rod, tube, capillary, fiber, strip, disc, plate, cuvette and the like, although the present invention contemplates supporting each surface on a separate mechanical support. The surface may form an integral part of the support or be distinct from the support, typically forming an applied layer on the support or spaced apart from the support and supported by two or more spacers.

The surface will typically be porous, with various pore sizes employed, depending on the nature of the system. The surface may be polyfunctional or be capable of being polyfunctionalized, so as to permit covalent bonding of mips, as well as to permit bonding of other compounds which form a part of the signal producing system. The precise nature of the surface is discussed in detail in U.S. Pat. No. 4,299,916 to Litman, et al., incorporated herein by reference.

Binding of mips to the surface material to form the measurement and calibration surfaces may be by well-known techniques, commonly available in the literature. See, for example, "Immobilized Enzymes," Ichiro Chibata, Halsted Press, New York (1978) and Cuatrecasas, *J. Bio. Chem.,* 245:3059 (1970).

A wide variety of organic and inorganic polymers, both natural and synthetic, and combinations thereof, may be employed as the material for the solid surface. Illustrative polymers include polyethylene, polypropylene, poly(4-methylbutene), polystyrene, polymethacrylate, poly(ethylene terephthalate), rayon, nylon, poly(vinyl butyrate), silicones, polyformaldehyde, cellulose, cellulose acetate, nitrocellulose, etc. Other materials which may be employed include paper, glasses, ceramics, metals, metaloids, semiconductive materials, cermets, silicates or the like. In addition are included substrates that form gels, such as proteins, e.g., gelatins, lipopolysccharides, silicates, agarose; and polyacrylamides or polymers which form several aqueous phases, such as dextrans, polyalkylene glycols (alkylene of 2 to 3 carbon atoms) or surfactants, e.g., amphiphilic compounds, such as phospholipids, long chain (12-24 carbon atoms) alkyl ammonium salts and the like.

The present device may also include a second catalyst bound to the surface where two catalysts are employed in the signal producing system. Typically, these catalysts are enzymes and binding of the enzyme to the surface may be carried out according to techniques well-known in the art.

Method

The simultaneous calibration assay is described in U.S. Ser. No. 374,849, filed May 4, 1982. The assay is carried out in an aqueous zone or medium, where the final assay medium may be the result of prior individual additions of reagents or combinations of reagents and incubations, prior separations involving removal of surfaces from an aqueous medium and transfer to a different aqueous medium having one or more reagents, or combinations thereof. While the subject method does not require a separation of labeled conjugate which is unbound from that which is bound to one or both surfaces through mip complexes, in many protocols a developer solution will be employed which is substantially free of unbound catalyst. The various media involved in the assay consist of a liquid phase and a solid phase which defines both the measurement and calibration "surfaces."

In carrying out the assay, the surfaces will be contacted by the sample, and by the members of the signal producing system, and any ancillary materials, in an aqueous medium, either concurrently or stepwise, to provide a detectable signal associated with the surfaces. The detectable signal at the measurement surface will be related to the amount of the labeled conjugate bound to that surface, which relates to the amount of analyte in the sample. Depending upon the nature of the signal producing system and the desired method for detecting the signal, the surfaces may be read in the assay medium or will be read separate from the assay medium.

In carrying out the assay, an aqueous medium will normally be employed. Other polar solvents may also be included, usually oxygenated organic solvents of from 1–6, more usually from 1–4 carbon atoms, including alcohols, ethers and the like. Usually these cosolvents will be present in less than about 40 weight percent, more usually in less than about 20 weight percent.

The pH for the medium will usually be in the range of about 4–11, more usually in the range of about 5–10, and preferably in the range of about 6.5–9.5. The pH is chosen so as to maintain a significant level of specific binding by the receptor while optimizing signal producing efficiency. In some instances, a compromise will be made between these two considerations. Various buffers may be used to achieve the desired pH and maintain the pH during the determination. Illustrative buffers include borate, phosphate, carbonate, tris, barbital and the like. The particular buffer employed is not critical to this invention but in individual assays, one buffer may be preferred over another.

Moderate temperatures are normally employed for carrying out the assay. Constant temperatures during the period of the measurement are generally not required, but rapid and large fluctuations are not desirable. The temperatures for the determination will generally range from about $10°-50°$ C., more usually from about $15°-45°$ C.

The concentration of analyte which may be assayed will generally vary from about $10^{-4}$ to $10^{-15}$ M, more usually from about $10^{-6}$ to $10^{-13}$ M. Considerations such as whether the assay is qualitative, semi-quantitative or quantitative, the particular detection technique and the concentration of the analyte of interest will normally determine the concentration of the other reagents.

The concentration of various reagents will vary widely depending upon which protocols are employed, the nature of the analyte, the mip which is bound to the surface and the mip which is bound to the catalyst, the required sensitivity of the assay, and the like. In some instances, large excesses of one or the other of the mips may be employed, while in some protocols the sensitivity of the assay will be responsive to variations in the mip ratios In carrying out the simultaneous calibration assay, it is necessary that both the measurement and calibration surfaces be contacted simultaneously with the sample and the signal producing system. It is also desirable that both surfaces be located close to one another, while they are immersed in the assay medium, to minimize any differences which might result from local variations in the medium. Conveniently, this may be accomplished by mounting both surfaces on a common rod or support. Mounting of the surfaces on a common support, however, is not required to practice the method of the present invention and it is necessary only that the surfaces be immersed in the various components of the signal producing system and sampled at the same time and for identical lengths of time. The surfaces may otherwise be handled independently without having an adverse effect on performance of the assay.

The common support for the surfaces is conveniently a rod or plastic film as used in the immunochemical strips of the prior art. The precise nature and dimensions of such strips are not critical and may be chosen to conform with other components of the assay system, typically the sizes of the various reagent containers. It is desirable that both surfaces be placed at one end of an elongate strip so that they may be easily immersed in a relatively small sample, typically 100 $\mu$l to 2 ml. Mounting the surfaces adjacent each other also facilitates visual comparison of the surfaces to perform the final determination. The surfaces may be vertically or horizontally positioned.

As already indicated, more than two surfaces may be employed, involving either or both a plurality of measurement surfaces and a plurality of calibration surfaces. For example, a plurality of analytes may be simultaneously determined and/or a plurality of calibration surfaces provided to provide for a more quantitative result or a different calibration surface associated with each of the measurement surfaces for the different analytes.

A wide variety of protocols may be involved, where one or more solutions will be employed. Contact with the solutions may involve agitation or standing. Incubation steps may be involved, generally varying from about 0.5 minutes to 1 hour, more usually from about 2 minutes to 30 minutes. Depending upon the various protocols: (1) all of the materials involved in the assay may be combined with the sample; (2) the catalyst reagent may be combined with the sample, while one or more substrates are combined in a separate solution, referred to as the developer solution, where the surfaces are transferred from solution to solution; or (3) the sample, catalyst reagent and at least a portion of the substrates combined in one solution, while the remaining substrates combined in another solution, where the surfaces are transferred from solution to solution. Normally, wash steps are not required between transfers since little interference is observed as a result of any adventitious non-specific binding. Competitive and non-competitive protocols may be employed. The analyte and the catalyst labeled analyte may compete for homologous mip on the measurement surface or they may successively bind. Where the analyte has a plurality of binding sites, it may serve as a bridge between the mip bound to the measurement surface and the mip of the catalyst labeled analyte. By varying (1) the various mips on the surface and those involved in the catalyst conjugate, (2) the number of solutions with which the surfaces are contacted, and (3) the members of the signal producing system, the protocols can be varied widely, depending upon the degree of quantitation desired, the sophistication of the user, and available equipment.

In systems involving a single catalyst, usually an enzyme, the catalyst-bound-mip and analyte can be employed in a competitive mode, where the catalyst-bound-mip competes concurrently or consecutively for the homologous mip at the measurement surface. Thus, one could have the surfaces contact the sample containing the analyte either in combination with the catalyst-bound-mip or followed by contact with the catalyst-bound-mip. In the former case, the catalyst-bound-mip is in relatively limited amount and directly competes with the analyte for available mip binding sites on the measurement surface. In the latter case, the catalyst-bound-mip fills available binding sites which remain after binding of analyte to the measurement surface and, therefore, can be in greater excess of the analyte concentration of interest than in the former situation. After sufficient time for the mips to bind to the measurement surface, the surfaces may then be contacted with the appropriate substrates and cofactors which include a compound which results in a product which will bind to the surfaces and provide a detectable signal.

Alternatively, a combination of catalysts, particularly having at least one enzyme, may be employed, where one of the catalysts produces a product which is the substrate of the other catalyst. This system is preferred, particularly with two enzymes, in that it minimizes the number of reagent solutions required and/or washing requirements and provides for rapid production of the signal generating compound at the surfaces. In this embodiment, the measurement surface includes not only a mip, but also one of the two enzymes, preferably the first enzyme in the series. The enzyme-bound-mip is preferably the second enzyme in the series. The product of the first enzyme is an essential substrate for the second enzyme, so that the various substrates and cofactors necessary for the signal producing system may be combined with the second enzyme without concern as to premature reaction in an aqueous medium. Only upon combination with the surfaces will the substrate of the first enzyme be turned over to provide the product which is the substrate of the second enzyme.

In the simplest protocol, one would have all the reagents combined in an appropriate formulation, conveniently a lyophilized powder formulation, which is dissolved in a measured amount of an aqueous medium containing the sample. After a sufficient time for the solution to become homogeneous, the surfaces may be introduced into the sample solution, where the signal producing system involves two enzymes, related by one enzyme producing a product which is the substrate of the other enzyme. By having the first enzyme bound to both the measuring surface and the calibration surface, one can combine the second enzyme with the substrate for the first enzyme without concern about premature reaction, since until the first enzyme produces the necessary substrate for the second enzyme, there will be no reaction. Where only a single catalyst is employed in the signal producing system, it will normally be necessary to have at least two solutions with separate contacting of the surfaces with the two solutions, one of the solutions having the substrate for the catalyst and the other solution having the catalyst-bound-mip.

The signal generating compound may provide an increase or decrease in the observed signal. The signal generating compound will preferentially bind to the surfaces and provide a detectable signal, which may be visually detected, or detected by a reflectometer or fluorometer. The signal generating compound will normally be substantially insoluble in the medium in which it is produced and will be derived either directly or indirectly from a catalytic product. By having the signal generating compound produced adjacent to the surfaces by the presence of catalyst bound to the surfaces, the proportion of the total signal generating compound resulting from binding of the signal generating compound to the surfaces from the bulk solution will be minimized.

In a number of situations, a scavenger may be desirable. For example, where the two enzymes are used in the signal producing system, by having a scavenger in the bulk solution for the product of the first enzyme, production of the signal generating compound in the bulk medium can be further reduced. Also, where the signal generating compound is produced in the presence of unbound enzyme-bound-mip in the bulk medium, a scavenger for the signal generating compound in the bulk medium may be useful. Alternatively, an enzyme inhibitor may be employed, which selectively deactivates the enzyme in solution but is substantially inactive toward the enzyme bound to the surface. This can be achieved by employing reversible inhibitors or suicide inhibitors bound to a large porous particle which inhibits access of the inhibitor bound to the particle to the binding site of the enzyme bound to the surface.

For the most part, the signal generating compound will enhance the signal at the surface. However, there is also the possibility for reducing the signal at the surface. For example, where the surface is fluorescent, one can provide for production of quencher which will diminish the surface fluorescence. Alternatively, one could have the surface colored with one dye, where the observed coloration would change upon precipitation of a different dye upon the surface. Alternatively, one could employ a combination of enzymes, where the first enzyme produces a signal generating compound and the second enzyme destroys the signal generating compound, or an essential intermediate is destroyed. For example, by having glucose oxidase and horse radish peroxidase on the surface, with catalase bound to a mip, the more catalase which binds to the surface, the less dye that would be produced. Thus, by having a second enzyme present as the enzyme-bound-mip, the amount of enzyme-bound-mip which binds to a surface would be related to the decrease in the observed production of the signal generating compound.

For quantitation, one can develop a ratio of signal level on the measurement surface as related to the signal level on the calibration surface. Thus, by providing for a particular time period from the initiation of production of a signal generating compound to termination of further production of the signal generating compound, the ratio of the signal from the measurement surface and calibration surface can be related to standard values for quantitating the amount of analyte. The time is not a critical factor, so long as a sufficient change in signal occurs at both the measurement surface and calibration surface, but not so long that a change in signal can no longer be observed at the surfaces. Thus, the ratio will provide a result which is relatively insensitive to time, temperature and endogenous interference.

The following is an exemplary protocol. A combination of enzymes is used which will allow for a single formulation and a single contacting of the sample and reagent solution with the surfaces for production of the signal generating compound. A hapten which corresponds to the analyte is conjugated to an enzyme. The measurement surface will have antibody specific for the hapten, while the calibration surface in accordance with the present invention will have an antibody, as a conjugate receptor, specific for the conjugate of the catalyst and the hapten, which antibody is substantially incapable of binding with the catalyst or the mip apart from the conjugate. The conjugate receptor on the calibration surface is present in a predetermined amount to provide for production of signal generating compound independent of the amount of analyte in the assay medium. In addition to the antibodies, the surfaces will also have comparable amounts of a first enzyme which produces a product which is a substrate for the enzyme of the enzyme-bound-ligand.

In the exemplary protocol, the amount of catalyst-bound-mip which binds to the calibration surface will not be a function of the amount of analyte in the medium. Since the catalyst-bound-mip will not react with the substrate provided for in the assay medium, in the absence of the product of the enzyme bound to the surface, all of the reagents may be combined in a single formulation which may then be combined with the sample. The catalyst-bound-mip which competes with the analyte for the mip on the measurement surface will be in limited amount, so as to allow for variation in the amount of catalyst-bound-ligand which binds to the measurement surface in relation to varying amounts of analyte present in the medium. As previously indicated, the formulation may include buffers, stabilizers, excipients, and the like, in addition to the catalyst-bound-mip and substrates.

The formulation may be first dissolved in an aqueous medium to provide a solution having the reagents at the appropriate concentrations. An aliquot of the solution may be taken of a predetermined volume and a sample measured into the solution. Since the first enzyme is essential for the enzymatic reaction to proceed, the surfaces are then introduced into the solution and a sufficient time allowed for the signal generating compound to form at the surfaces, at which time the surfaces are removed. The surfaces are visually inspected or the level of signal generation determined by an appropriate apparatus.

Since the signal level of the calibration surface is independent of the analyte concentration, one can provide that for a signal level at the measurement surface greater than the signal level at the calibration surface, the analyte will be present in greater than a predetermined amount. Alternatively, by employing ratios of the signal levels of the measurement surface and calibrator surface and comparing these to standards prepared employing known amounts of analyte, one can quantitate the amount of analyte present in the sample.

For a description of various techniques which find application in the subject invention, see U.S. Ser. No. 374,849, filed May 4, 1982, and U.S. Pat. No. 4,299,916, Cols. 7-16, which subject matter is incorporated herein by reference.

EXAMPLES

The following examples are offered by way of illustration and not by way of limitation.

All percents and parts not otherwise indicated are by weight, except for mixtures of liquids which are by volume. When the solvent is not indicated, water is intended. All temperatures not otherwise indicated are centigrade. The following abbreviations are employed: PA—penicilloic acid; HRP—horse radish peroxidase; NHS—N-hydroxy succinimide; EDCI—N-ethyl-N'-(3-dimethylaminopropyl) carbodiimide; DMF—N,N-dimethyl formamide; THF—tetrahydrofuran; BSA—bovine serum albumin; GO-AMINE—glucose oxidase-amine; Triton QS 44—anionic surfactant (Rohm and Haas Co.); NaAZ—Sodium azide; CDI—1,1'-Carbonyl diimidazole, EDTA—ethylenediaminetetraacetic acid.

EXAMPLE 1

Preparation of Anti-PA Paper

The following experiments employed anti-PA coupled to a paper support prepared in bulk as follows: Whatman 1C Paper (16 feet × 10.63 inches) was rolled on a one-inch diameter spool with two screens separating adjacent layers of paper to allow penetration by reagents. The resulting cartridge was inserted into a reactor where it was dried with nitrogen overnight. CDI (85 gm Polysciences, Lot No. 12087, Catalog No. 15750) was dissolved in 2.5 l. of dichloromethane. The solution was recirculated through the reactor with a centrifugal pump at a flow rate of approximately 4 l./minute for two hours. The paper was then washed three times with dichloromethane (2.5l.) and dried with nitrogen (approximately 7 l./minute) for three hours and stored at room temperature overnight.

A mixture of antibody to PA (0.2 mg/ml) and GO-AMINE (0.1 mg/ml) in phosphate buffer (2.8 l.) at 24° C. was recirculated through the reactor at approximately 2 l./minute for four hours. The paper was then washed four times with phosphate buffer (4 l.) and stabilized with 2.5 l. of a solution containing sucrose (15%) and BSA (2 mg/ml). Excess fluid was removed with nitrogen (40 psi for 1 min, 80 psi for 15 sec). The paper was then dried with heated air in a tunnel dryer.

EXAMPLE 2

Preparation of Monoclonal Anti-(HRP-PA) Paper

A. Preparation of monoclonal anti-(HRP-PA)

A conjugate of PA-BSA was prepared as follows: One hundred mg of BSA was suspended in 10 ml of 0.15 M NaCl. To this was added 300 mg of PA. The pH of the solution was adjusted to 10 by the careful addition of 10 N NaOH. This mixture was incubated at 37°, and sufficient base was added to maintain the pH at around 10. The incubation was allowed to proceed overnight. After incubation, the material was dialyzed extensively against 0.15 M NaCl to obtain the PA-BSA conjugate which was injected into mice.

The myeloma cell NS-1 (P3-NSl-1) ("HAT" selectable) was collected in log growth phase, $10^7$ cells washed and diluted into 20 m of Dulbecco's Modified Eagle Medium (DMEM). Mouse spleens were aseptically removed, the spleen disrupted in a 7 ml glass-bore tissue homogenizer, and the cellular dispersion added directly to the NS-1 cells. The cellular mixture was centrifuged, washed × 3 with DMEM, and then resuspended in 2 ml of 38 percent (w/v) polyethylene glycol (PEG-1540) in DMEM. The suspension was then centrifuged at gradually increasing force 250 × g for 2 min, 500 × g for 2 min, and 1000 × g for 2 min. The supernatant was carefully removed and the pellet gently resuspended in 6 ml DMEM supplemented with 15 percent fetal calf serum, 10 percent NCTC 109 (thymidine hypoxanthine supplement, Microbiological Assoc.), 0.2 μg bovine insulin/ml, 0.45 mM pyruvate, 1 mM oxaloacetate, 2 mM L-glutamine, and 50 mg/ml gentamicin. Cells were centrifuged, the pellet washed once, and resuspended in 100 ml "HAT" selective medium (supplemented DMEM+0.1 mM hypoxanthine, 0.01 mM aminopterin, 0.016 mM thymidine). The suspension was plated into 10 96-well plates. The cells were fed with the "HAT" medium on day 7 with additional feedings on days 9 and 14.

An ELISA assay was employed to screen the supernatants from hybridomas. Into each well (Costar EIA plate, 96 wells) successively introduced and flicked out: 10 μl of 10 μg PA-HRP for 2 hr at 37° C., 100 μl culture supernatant for 1 hr at 37° C. The plates were then washed 3 × PBS+0.05 percent Tween 20. Anti-mouse polyclonal antibody (100 μl, 1 μg/ml) conjugated to alkaline phosphatase was added and incubated for 1 hr at 37° C. and washed 3 × with PBS-Tween 20. Finally, 100 μl of 0.6 mg/ml p-nitrophenyl phosphate in substrate buffer (0.098 g MgCl₂ H₂O, 192 ml ethanolamine;

H₂O to 2L, pH 9.8). Optical densities (ODs) were read at 405 nm on a 96-well Titertek reader (Flow Labs). An ELISA(+) colony was isolated and cloned to give a cell line designated Pen A VII-33 producing the desired anti-(HRP-PA) used in the experiments below.

B. Two rolls of filter paper were prepared with monoclonal anti-(HRP-PA) as follows:

A first roll of Whatman 1C Paper (12 feet×10.63 inches) was rolled on a two-inch diameter spool with a pair of wire screens separating adjacent layers. A second roll of Whatman 1C paper (16 feet×10.63 inches) was rolled on a one-inch diameter spool, also with adjacent layers separated by a pair of wire screens. The first roll was placed in a first reactor and the second roll was placed in a second reactor, where both rolls were dried under vacuum overnight with nitrogen bleeding to remove moisture.

CDI (170 gm) was dissolved in 5.0 l. of dichloromethane, which was recirculated at 4 l./min through the reactors connected in series. The papers were then washed three times with 4.5 l. of dichloromethane, and then dried for three hours with nitrogen (6 l./min) and overnight at 200 ml/min.

Paper from the second reactor was treated with a mixture of monoclonal antibody to HRP-PA (220, 110, 44, 22, 11, and 2.2 µg/ml), non-immune sheep IgG (222 µg/ml), GO-Amine (0.2 mg/ml)(see below for preparation) and QS44 (2%,W/V) in phosphate buffer adjusted to pH6.94 with 1.0 M NaOH. The mixture was incubated overnight with stirring.

The papers were then washed four times with phosphate buffer (500 ml) and stabilized with (500 ml) of sucrose (15%) and BSA (2 mg/ml). Excess fluid was removed by blotting and the paper was dried in a convection oven at 50° C. for 10 minutes.

Glucose oxidase (Sigma, E.C. 1.1.3.4) was concentrated from 360 ml to 60 ml with Amicon PM10 membrane at a pressure below 30 psi. The concentrate of glucose oxidase was dialyzed twice against 4 l. of water at 4°, filtered and shown spectrophotometrically to have a concentration of 32 mg/ml. To 51.5 ml of the glucose oxidase solution was added dropwise 5.15 ml 0.2 M sodium periodate, the reaction occurring over 25 minutes. The product was chromatographed on a 2.5×60 cm column of Sephadex G-50 using 2 mM sodium acetate pH 4.5, and the major glucose oxidase peaks pooled to yield 91.5 ml of a solution containing the aldehyde derivative. To the solution was added dropwise 6 ml of 3 M ethylene diamine in 0.2 M sodium carbonate, pH 9.5, and the reaction allowed to proceed for 3 hours. To the mix was then added about 3.9 ml of 10 mg/ml sodium borohydride, the mixture incubated overnight and then chromatographed to remove the sodium borohydride.

EXAMPLE 3

Conjugation of PA to HRP

To 2 ml of 8.24 mg/ml HRP in water was added, 0.5 ml of 0.0124 M sodium periodate, and the mixture was stirred for one hour. The mixture was subjected to chromatography on a Sephadex PD-10 column, eluting with 5 mM acetate buffer, pH 4.5. The protein fractions were pooled to give 3.5 mls.

To the pooled oxidized -HRP fractions was added, 0.5 ml of 2 M phosphate buffer, pH 7.0, containing 38.5 mg ampicillinoic acid. The reaction was stirred for 30 minutes at room temperature; then 0.65 ml of a 10 mg/ml sodium cyanoborohydride solution was added with stirring. The reaction was incubated overnight at 4° and was then dialyzed extensively against 0.1 M phosphate, 0.2 M sodium chloride, pH 7.0.

EXAMPLE 4

Preparation of Immunochemical Strips

For use in assays, ¼ inch discs were punched in the anti-PA paper of Example 1 and the anti-(HRP-PA) paper of Example 2. The discs (one of each) were then attached side-by-side to one end of a plastic stick to form the immunochemical strip.

EXAMPLE 5

Color Development of Anti-(HRP-PA) Papers

The assay protocol involved incubation of the sample with penicillin, addition of the immunochemical test strip, and then addition of the color generating developer. The sample was extracted into a diluent containing 0.15 M saline, 1 mM EDTA and 0.2 mg/ml BSA. For the laboratory assay, $10^{-3}$ International Units per test of β-lactamase was used for the positive sample. The color generating solution (developer) consisted of 50 mM phosphate, 0.005% triton QS44, 2 mg/ml BSA pH 7.0, plus 50 mM glucose, 0.3 mg/ml 4-chloro-1-naphthol, and 250 µg/ml HRP-PA.

To a 5 ml vial containing 20 µg penicillin and bulked with mannitol powder, 2 mls of sample diluent with or without β-lactamase was added. The penicillin plus the sample was incubated for 15 minutes at 43° in a circulating water bath. The immunochemical test strip was then agitated in the solution for 5 seconds, followed by the addition of 2 ml of developer. The sample test strip developer solution combination was incubated for an additional 10 minutes at 43°. The test strip was then removed and blotted, and the color intensity was determined using a Macbeth MS 2000 Reflectance Spectrophotometer. Data were reported relative to a standard which was a white ceramic chip.

EXAMPLE 6

Standard Curve as a Function of HRP Concentration

The protocol described in Example 5 was followed employing both anti-(HRP-PA) and anti-PA papers. The β-lactamase concentration employed was 0, $10^{-3}$, and $10^{-1}$ Iu (International units) per milliliter (ml). The results are summarized in the table below:

| β-lactamase | Color development (c.u.)* | |
| (Iu/ml) | Anti-(HRP-PA) | Anti-PA |
| --- | --- | --- |
| 0 | 36 | 32.5 |
| $10^{-3}$ | 35.4 | 19.0 |
| $10^{-1}$ | 31.2 | 16.6 |

*c.u. = color unit, one color unit being defined as

The above data indicate that the penicilloic acid (PA) produced by the reaction of β-lactamase with penicillin G sharply reduces color development with the anti-PA paper but has minimal effect on the anti-(HPP-PA).

EXAMPLE 7

Standard Curve as a Function of PA Concentration

The protocol described in Example 5 was followed except that PA was added instead of β-lactamase and penicillin G. The concentration of PA was 0, 1.0, 10.0, 100.0, and 1000.0 μ/ml, respectively. The results are summarized in the table below.

| PA (μg/ml) | Color Development (c.u.) |
|---|---|
| 0 | 33.8 |
| 1.0 | 32.0 |
| 10.0 | 32.2 |
| 100.0 | 24.5 |
| 1000.0 | 13.3 |

The above data indicate that color development on anti-(HAP-PA) paper is not significantly affected until the concentration of PA reaches 100.0 μg/ml.

EXAMPLE 8

The protocol described in Example 5 was followed employing both anti-(HRP-PA) and anti-PA papers with the exception that HPP-PA concentration was varied. The concentration of HRP-PA was 150, 250, and 250 mg/ml, respectively. The results are summarized in the table below:

| HRP-PA (mg/ml) | Color development (c.u.) | |
|---|---|---|
| | Anti-(HRP-PA) | Anti-PA |
| 150 | 30.3 | 26.2 |
| 250 | 36.1 | 32.5 |
| 250 | 34.0 | 31.6 |

The above results indicate that the level of color development for the anti-(HRP-PA) paper exceeds that for the anti-PA paper at equivalent levels of HRP-PA.

EXAMPLE 9

The protocol described in Example 5 was followed employing anti-(HRP-PA), anti-PA, and anti-HRP papers. HRP-PA conjugate which had been stored at room temperature for about 9 months was employed in place of the freshly prepared conjugate used in Example 5. The stored conjugate was found to be ineffective in an assay. β-Lactamase was either omitted or was present at a concentration of $10^{-3}$ Iu/ml. The results are summarized in the following table.

| β-lactamase (Iu/ml) | Color development (c.u.) | | |
|---|---|---|---|
| | Anti-(HRP-PA) | Anti-PA | Anti-HRP |
| $10^{-3}$ | 7.9 | 8.4 | 14.6 |
| 0 | 8.8 | 9.9 | 17.1 |

The above data indicate that when the HRP-PA conjugate degrades, the color development of the anti-PA and anti-(HRP-PA) papers decrease by the same intensity, but the color development of the anti-HRP paper is less affected.

What is claimed is:

1. In a method for determining the presence in a sample of an analyte, which analyte is a member of a specific binding pair ("mip") consisting of ligand and receptor ("antiligand"), said method comprising the step of:
(a) contacting with said sample (i) at least one enzyme including an enzyme bound to a mip ("enzyme-bound-mip") and (ii) a solute which is catalytically transformed by an enzyme bound to a mip-containing measurement first surface to produce a change in a detectable signal at said first surface in proportion to the amount of enzyme-bound-mip bound to said first surface, wherein said enzyme-bound-mip binds to said first surface in proportion to the amount of analyte in said sample, and (iii) a calibration second surface, adjacent to said first surface to which second surface enzyme becomes bound in an amount which provides substantially predetermined ratios to the amount of said enzyme bound to said first surface, whereby the intensity of the signal at said second surface compared to the intensity of signal at said first surface is related to the amount of analyte in said sample, and
(b) determining said signal,
the improvement which comprises employing on said second surface a receptor for said enzyme-bound-mip, said receptor being capable of specific binding to said enzyme-bound-mip and being substantially incapable of binding to said enzyme or said mip part from said enzyme-bound-mip.

2. The method of claim 1 wherein said receptor for enzyme-bound-mip is capable of specific binding to a site on the enzyme-bound-mip comprising the group linking the enzyme to the mip in the ' enzyme-bound-mip.

3. The method of claim 1 wherein said receptor for enzyme-bound-mip is an antibody.

4. The method of claim 1 wherein said receptor for enzyme-bound-mip is a monoclonal antibody.

5. In a method for determining the presence in a sample of an analyte, which analyte is a member of a specific binding pair ("mip") consisting of ligand and receptor ("antiligand"), said method comprising the steps of
(a) contacting with said sample (i) a signal producing system having at least two enzymes, including one enzyme bound to a mip ("enzyme-bound-mip"), and (ii) a solute dye precursor which is catalytically transformed to an insoluble dye by one of said enzymes bound to a mip-containing measurement first surface, said insoluble dye producing a change in a detactable signal at said first surface in proportion to the amount of analyte, where said mip at said first surface provides for binding of enzyme-bound-mip through mip complex formation to said first surface and said enzyme-bound-mip binds to said first surface in proportion to the amount of analyte in said sample, and (iii) a calibration second surface, adjacent to said first surface, to which second surface enzyme of said enzyme-bound-mip becomes bound through mip complex formation in an amount which provides substantially predetermined ratios to the amount of enzyme-bound-mip on said first surface, where the intensity of the signal at said second surface compared to the intensity of signal at said first surface is related to the amount of analyte in said sample, and
(b) determining said signal,
the improvement which comprises employing on said second surface a receptor for said enzyme-bound-mip, said receptor being capable of specific binding to said enzyme-bound-mip and being substantially incapable of binding to said enzyme or said mip apart from said enzyme-bound-mip.

6. The method of claim 5 wherein said receptor for enzyme-bound-mip is capable of specific binding to a site on the enzyme-bound-mip comprising the group linking the enzyme mip in the enzyme-bound-mip.

7. The method of claim 5 wherein said receptor for enzyme-bound-mip is an antibody.

8. The method of claim 5 wherein said receptor is a monoclonal antibody.

9. A method for determining the presence in a sample of an analyte, which analyte is a member of a specific binding pair ("mip") consisting of ligand and receptor ("antiligand"), which method comprises the steps of
    (a) contacting an enzyme bound to a mip ("enzyme-bound-mip"), a solute which is catalytically transformed by an enzyme, and said sample with a measurement surface containing a mip and an enzyme different from that of the enzyme-bound-mip, and a calibration surface, adjacent to said measurement surface, containing enzyme different from that of the enzyme-bound-mip and an antibody specific for said enzyme-bound-mip, said antibody being capable of specific binding to said enzyme-bound-mip and being substantially incapable of binding to said enzyme or said mip apart from said enzyme-bound-mip, wherein the enzymes are related by the product of one being the substrate of the other, and
    (b) measuring a change in a detectable signal at said measurement surface, wherein said enzyme-bound-mip becomes bound to said calibration surface in an amount which provides substantially predetermined ratios to the amount of said enzyme bound to said measurement surface, whereby the intensity of the signal at said calibration surface compared to the intensity of signal at said measurement surface is related to the amount of analyte in said sample.

10. The method of claim 9 wherein said antibody specific for said enzyme-bound-mip is a monoclonal antibody capable of specific binding to a site on said enzyme-bound-mip comprising the group linking the enzyme and the mip.

11. The method of claim 9 wherein the enzyme of said enzyme-bound-mip is horse radish peroxidase and the enzyme bound to said measurement and calibration surfaces is glucose oxidase.

12. A device for use in the method of claim 1 which comprises a surface to which a receptor is non-diffusively bound, said receptor being capable of specific binding to a conjugate of the enzyme and the mip and being substantially incapable of binding to the enzyme or the mip apart from the conjugate.

13. The device of claim 12 which further includes an enzyme bound to said surface.

14. A internally calibrated diagnostic device comprising a support, a measurement surface of a porous material, a calibration surface of a porous material in close proximity to said measurement surface, a member of a specific binding pair ("mip") non-diffusively bound to said measurement surface, and a receptor non-diffusively bound to said calibration surface, said receptor being capable of specific binding to a conjugate of an enzyme and a mip but substantially incapable of binding to said enzyme or said mip apart from said conjugate.

15. The devices of claim 14 wherein said receptor for enzyme-bound-mip is capable of specific binding to a site on the enzyme-bound-mip comprising the group linking the enzyme to the mip in the enzyme-bound-mip.

16. The devices of claim 14 wherein said receptor for enzyme-bound-mip is an antibody.

17. The device of claim 14 wherein said receptor is a monoclonal antibody.

18. The devices of claim 14 wherein said mesurement and calibration surfaces further include an enzyme different from that of the enzyme-bound-mip, wherein the two enzymes are related by the product of one being the substrate of the other.

19. The device of claim 18 wherein the enzyme of said enzyme-bound-mip is horse radish peroxidase and the enzyme bound to said measurement and calibration surfaces is glucose oxidase.

* * * * *